United States Patent [19]

Meyer et al.

[11] 4,035,238
[45] July 12, 1977

[54] STAPHYLOCOCCUS AUREUS BROTH

[75] Inventors: Michael C. Meyer, O'Fallon, Ill.; Clifton Aldridge, Maryland Heights, Mo.

[73] Assignee: McDonnell Douglas Corporation, St. Louis, Mo.

[21] Appl. No.: 682,656

[22] Filed: May 3, 1976

[51] Int. Cl.$^2$ .......................................... C12K 1/10
[52] U.S. Cl. ......................... 195/100; 195/103.5 M
[58] Field of Search ............ 195/99, 100, 101, 102, 195/103, 103.5 R

[56] References Cited
PUBLICATIONS

Robert Bailey and Eliryn Scott; Diagnostic Microbiology; Second Ed.; the C.V. Mosby Company; 1966; pp. 26, 295 and 296.

*Primary Examiner*—Alvin E. Tanenholtz
*Assistant Examiner*—Robert J. Warden
*Attorney, Agent, or Firm*—Gravely, Lieder & Woodruff

[57] ABSTRACT

A broth medium for the detection of *Staphylococcus aureus* in urine. The medium employs mannitol to promote growth of *S. aureus*, potassium tellurite to inhibit growth of gram-negative organisms, amphotericin B to inhibit growth of yeast, and DNA methyl green indicator.

13 Claims, No Drawings

STAPHYLOCOCCUS AUREUS BROTH

BACKGROUND OF THE INVENTION

*Staphylococcus aureus* (*S. aureus*) is a microorganism which occurs in urine, abcesses, etc. The presence of this microorganism in urine is a reliable indicator of urinary infection. If *S. aureus* is present in a given sample of urine, it is also possible that *E. coli*, *Streptococeus*, and other like organisms are also present.

The medium of this invention is an improved medium designed for use with the optical detection system disclosed in U.S. application Ser. Nos. 255,533 filed May 22, 1972 now abandoned and 461,249 filed Apr. 16, 1974 now U.S. Pat. No. 3,963,355 and in the improved devices disclosed and claimed in applications filed on even date herewith by Charles, Jones, Staples and Wiegner entitled AUTOMATED MICROBIAL ANALYZER and MACHINE AND PROCESS FOR READING CARDS CONTAINING MEDICAL SPECIMENS. These applications describe mechanism and apparatus suitable for analyzing specimens for specific microorganisms using a plastic tray or card which contains a series of dried culture media contained in separate but connected cells, each of the media being specific to a single organism. When the sample is inserted into the card, mixed with the media in the cells, and incubated in the machine, the organism (or organisms) present in the specimen interacts with the culture medium specific to that organism and produces a change in the medium which is read by the machine to indicate the presence of that organism. The change in the medium involves a change in the light transmitting properties of the medium, i.e., a color change or change in turbidity. The change may be caused by metabolic activity of the organism, which, for example, may cause production of acid and a change in pH which causes a color change in a pH sensitive indicator in the medium. The change in the light transmitting properties of the medium also could be caused by a precipitate forming in the medium due to metabolic activity of the organism or it could be caused by growth of the organism.

The specific media designed for use in the aforesaid cards are all designed to favor growth of one microorganism and to inhibit growth of other organisms, are capable of being freeze dried, and can function in the low $O_2$ environment of the wells of the card described in detail in said copending applications AUTOMATED MICROBIAL ANALYZER and MACHINE AND PROCESS FOR READING CARDS CONTAINING MEDICAL SPECIMENS.

We have discovered a medium which can selectively identify *Staphylococcus aureus* organism in urine when the medium is placed in the wells of the cards described in application AUTOMATED MICROBIAL ANALYZER.

Positive results are indicated by means of a change in color of an indicator solution incorporated into the medium which causes a change in the light transmitting character of the medium, which change is read by the mechanism described in application AUTOMATED MICROBIAL ANALYZER. The entire test can be completed within 12-18 hours, whereas current methods of detection require from 36 to 48 hours.

SUMMARY OF THE INVENTION

This invention involves a broth medium for the detection of *Staphylococcus aureus* in urine.

The medium contains mannitol, sodium chloride, potassium tellurite, amphotericin B and a biological indicator.

A novel feature of the invention lies in the color indicator system. DNA methyl green is used as the color indicator and the objective is to obtain a bluish color in the presence of *Staphylococcus aureus*, because the mechanism shown in application AUTOMATED MICROBIAL ANALYZER reads blue. The amount of DNA methyl green used is about 200 to about 400 mgm DNA methyl green per liter of medium.

In this invention the DNA methyl green is changed to a reddish purple by sequentially adding to a solution containing it Supplement VX from Difco and Vitamin B-12. When Supplement VX is added there is a lightening of the green color which is believed to be caused by a reducing material and when the red Vitamin B-12 is added the medium turns a reddish purple.

When *Staphylococcus aureus* is added to this reddish purple medium, it attacks the DNA methyl green and a bluish purple results, probably from a reaction of the methyl green with a protein or other large body in the medium. Normally in a reaction involving Staphylococcus and DNA methyl green, the color of the medium changes from green to colorless.

Potassium tellurite and amphotericin B are used to inhibit gram-negative organisms and yeast, respectively.

DETAILED DESCRIPTION

The detection broth of the present invention contains from 7.0 to 39.0% nutrients, about 0.055 to about 0.17% of an indicator which indicates the positive growth of *Staphylococcus aureus* organism, about 1.0 to about 3.0 ml/l potassium tellurite (1% stock solution), which operates as a biological inhibitor to inhibit the growth of gram-negative organisms, about 3 $\mu$g/ml to about 40 $\mu$g/ml amphotericin B, which operates as a biological inhibitor to inhibit growth of yeast, about 75 to about 95 gm/l sodium chloride to provide increased selectivity for *Staphylococcus aureus*. Sodium chloride also operates to inhibit growth of *Staphylococcus epidermidis* and *Streptococcus faecalis*.

The nutrient portion of the medium contains from about 0.25 to about 1.5 gm/l uracil, from about 5.0 to about 30.0 gm/l mannitol, from about 2.0 to about 7.5 gm/l Proteose Peptone No. 3, from about 2.0 to about 10.0 gm/l yeast extract, from about 5.0 to about 40.0 ml/l Supplement B, from about 30.0 to about 150.0 ml/l potassium oxalated rabbit plasma, and from about 30.0 to about 150.0 ml/l rabbit serum.

A suitable substitute for Proteose Peptone No. 3 is any peptone used in conventional broth media or any other suitable nitrogen source.

The purpose of the uracil is to aid the growth of *Staphylococcus aureus* in the low oxygen environment of the cards used in the mechanism of the application AUTOMATED MICROBIAL ANALYZER. The purpose of the mannitol is to provide a carbon source for *Staphylococcus aureus*. It is important that the medium be rich in nutrients to provide for rapid growth of *S. aureus*.

An important aspect of this invention is the action of the chemical inhibitors, potassium tellurite, sodium chloride and amphotericin B. These inhibitors act to inhibit the growth of organisms other than *Staphylococcus aureus*.

Growth of species of gram-negative organisms, yeast, *Staphylococcus epidermidis, Streptococcus faecalis* and other organisms which result in high yields of positives by conventional detection methods is inhibited by the presence of the foregoing chemical inhibitors in this broth.

The concentration of potassium tellurite (1% stock solution) can be from about 1.0 to about 3.0 ml/l, and it is most effective at 2.0 ml/l.

The concentration of amphotericin B can be from about 2500 to about 20,000 $\mu$g/l, and it is most effective at 5000 $\mu$g/l.

The concentration of sodium chloride can be from about 75 to about 95 gm/l, and it is most effective at 80 gm/l. If the concentration of any inhibitor is too low, a higher yield of unwanted false positives occurs. If the concentration is too high, a lower yield of positives occurs.

EXAMPLE I

To prepare a 2X medium in an amount of 100 ml, *Staphylococcus aureus* detection broth is prepared in the following manner:

47 ml of distilled water is placed in a graduated cylinder. One-half of this distilled water is heated to boiling and 0.1 gm uracil is dissolved therein. The uracil solution is cooled to 40° C. The remaining distilled water is added to the uracil solution. 4 ml of Supplement B (from Difco), 1.0 ml of 1,000 $\mu$g/ml stock solution of amphotericin B, and 16 gm of sodium chloride are added to the solution. The solution is stirred at 40° C until the sodium chloride is dissolved. 2.0 gm of mannitol, 1.0 gm of Proteose Peptone No. 3 (from Difco), 1.0 gm of yeast extract (from BBL), 0.4 ml of a 1% stock solution of potassium tellurite are added to the solution, and the pH is adjusted to 7.7. The solution is filter sterilized and stored in a covered container for 24 hours in a cold (2° C) room.

50 mg of DNA- methyl green is added to 20 ml distilled water and stirred in a covered container for 24 hours in a cold (2° C) room.

The DNA- methyl green solution is combined with the nutrient-inhibitor solution in a covered container. 10.0 ml of potassium oxalated rabbit plasma, 10.0 ml of rabbit serum, and 0.05 gm of Supplement VX (from Difco) are added to the mixture. The amount of Supplement VX used is about 0.15 to about 0.5 gm per liter of medium. See page 62 Difco 1975–76 Price List entitled *Culture Media and Reagents for Microbiological and Laboratory Procedure*. The mixture is then stirred for 10 minutes.

8.0 ml of a 1% stock solution of Vitamin B-12 is added to the solution. The amount of Vitamin B-12 used is about 0.2 to about 0.8 gm per liter of medium. (The 1% stock solution of Vitamin B-12 is prepared by mixing 0.1 gm Vitamin B-12, 9.2 ml distilled water, and 0.6 ml lN sodium hydroxide. The mixture is stirred for 10 minutes. The pH of the stock solution is adjusted to 8.0). Vitamin B-12 must be added last. The pH of the broth is then adjusted to 7.5 and centrifuged. The supernatant is poured into a sterile container and then stored.

The medium is at double (2X) the usual concentration for use in the wells and card described in application entitled AUTOMATED MICROBIAL ANALYZER.

What is claimed is:
1. A broth medium for the detection of *Staphylococcus aureus* comprising:
   a. a nitrogen source,
   b. a carbon source,
   c. biological nutrient sources,
   d. chemical inhibitors in an amount sufficient to inhibit growth of gram-negative organisms and yeast organisms but insufficient to inhibit *Staphylococcus aureus*, and
   e. a biological indicator comprising DNA methyl green and Vitamin B-12 in sufficient quantity so that the medium turns to a bluish color in the presence of *Staphylococcus aureus*.
2. The medium of claim 1 wherein the nitrogen source is uracil.
3. The medium of claim 2 including about 0.25 g/l to about 1.5 g/l uracil.
4. The medium of claim 2 wherein the carbon source is mannitol.
5. The medium of claim 4 including about 5 g/l to about 30 g/l mannitol.
6. The medium of claim 1 including the inorganic salt sodium chloride.
7. The medium of claim 6 wherein about 75 g/l to about 95 g/l sodium chloride is used.
8. The medium of claim 1 including potassium tellurite as a gram-negative inhibitor.
9. The medium of claim 8 wherein about 0.1 g/l to about 0.3 g/l potassium tellurite is used.
10. The medium of claim 1 wherein the yeast organism inhibitor is amphotericin B.
11. The medium of claim 10 wherein about 2500 to about 20,000 micrograms/l amphotericin B is used.
12. A broth medium for detection of Staphylococcus aureus comprising per liter of medium:
   a. about 0.2 to about 1.5 gm uracil,
   b. about 5 to about 30 gm mannitol,
   c. about 2 to about 7.5 gm Proteose Peptone No. 3,
   d. about 2 to about 10 gm yeast extract,
   e. about 5 to about 40 ml Supplement B,
   f. about 75 to about 95 gm sodium chloride,
   g. about 0.1 to about 0.3 gm potassium tellurite,
   h. about 2500 to about 20,000 Mgm amphotericin B,
   i. about 30 to about 150 ml potassium oxalated rabbit plasma,
   j. about 30 to about 150 ml rabbit serum,
   k. about 200 to about 400 mgm DNA methyl green,
   l. about 0.2 to about 0.8 gm Vitamin B-12, and
   m. said medium having a pH of about 7.5.
13. A broth medium for detection of Staphylococcus aureus comprising per liter of medium:
   a. 0.5 gm uracil,
   b. 10 gm mannitol,
   c. 5 gm Proteose Peptone No. 3,
   d. 5 gm yeast extract,
   e. 20 ml Supplement B,
   f. 80 gm sodium chloride,
   g. 0.2 gm potassium tellurite,
   h. 5,000 $\mu$gm amphotericin B,
   i. 50 ml potassium oxalated rabbit plasma,
   j. 50 ml Rabbit serum,
   k. 250 mgm DNA methyl green and,
   l. 0.4 gm Vitamin B-12,
   m. said medium having a pH of 7.5.

* * * * *